United States Patent [19]
Harrington

[11] Patent Number: 5,893,889
[45] Date of Patent: Apr. 13, 1999

[54] ARTIFICIAL DISC

[76] Inventor: Michael Harrington, 879 Smith St., Glen Ellyn, Ill. 60137

[21] Appl. No.: 08/879,410

[22] Filed: Jun. 20, 1997

[51] Int. Cl.$^6$ ........................................... A61F 2/44
[52] U.S. Cl. ................................. 623/17; 606/61
[58] Field of Search ................... 623/17, 18; 606/61

[56] References Cited

U.S. PATENT DOCUMENTS

| | | | |
|---|---|---|---|
| 5,360,430 | 11/1994 | Lin | 623/17 |
| 5,425,773 | 6/1995 | Boyd et al. | 623/17 |
| 5,458,642 | 10/1995 | Beer et al. | 623/17 |
| 5,674,296 | 10/1997 | Bryan et al. | 623/17 |
| 5,683,465 | 11/1997 | Shinn et al. | 623/17 |

FOREIGN PATENT DOCUMENTS

| | | | |
|---|---|---|---|
| 2263842 | 7/1974 | Germany | 623/17 |
| 0895433 | 1/1982 | U.S.S.R. | 623/17 |
| 9404100 | 3/1994 | WIPO | 623/17 |

*Primary Examiner*—Mickey Yu
*Assistant Examiner*—Bruce E. Snow
*Attorney, Agent, or Firm*—Robert L. Marsh

[57] ABSTRACT

A disc prosthesis for insertion between vertebrae of the spin has upper and lower members and a pivot ball retained in a socket to prevent the ball from becoming removed from the socket. Also, a shock absorbing member is fitted between the upper and lower member of the prosthesis. The upper and lower members are also vertically movable to compress the shock absorbing member and absorb shock in the spine.

6 Claims, 2 Drawing Sheets

ARTIFICIAL DISC

The present invention relates to a disc prosthesis for replacing discs between the vertebrae of the human spine.

BACKGROUND OF THE INVENTION

The spine is one of the most delicate portions of the human body, and is subject to failure from a number of causes, one of the most common being failure of a disc positioned between the vertebrae.

Prostheses have been successfully inserted between the vertebrae of the upper spine, but efforts to provide a prosthesis for the discs between the vertebrae of the lower spine have been less successful. Marnay, U.S. Pat. No. 5,314,477 and Salib, U.S. Pat. No. 5,258,031 are typical examples of current efforts to install such prostheses in lower vertebrae. These efforts, however, have not been successful for several reasons. First, existing prostheses have generally disc-shaped upper and lower members, each of which has outer dimensions nearly equal to the outer dimensions of the weight bearing portions of the upper and lower vertebrae, between which the original disc was positioned. To insert such a disc through a patient's back, an incision must be made between adjacent ribs. The disc must then be inserted without interfering with the spinal cord or any of its adjoining nerves. Surgeons have found that an incision large enough to receive a prosthesis cannot be made in the middle or lower back without causing damage to adjacent nerves.

A prosthesis disc might also be positioned between vertebrae of the middle and lower back by inserting it through the abdominal cavity, however, such efforts have also been unsuccessful. Extending along the back wall of the abdominal cavity are parallel arteries carrying blood to and from the lower extremities. Inserting a prosthesis disc through the abdominal cavity requires moving it between the arteries which run adjacent the inner surface of the back. Again, surgeons have been unable to safely insert existing prostheses through the abdomen.

Another problem of existing prostheses lies in their operation. Existing prostheses have upper and lower members, one of which has a generally semispherical portion which is received in a complementarily concave portion of the second member. Such prostheses employ the weight of the upper body to retain the semispherical portion of one member within the concave portion of the other member. When the patient is reclining, however, or when the patient bears his body weight with his arms so as to stretch the spine, existing prostheses are unable to retain their relationship to one another, and the parts may become disoriented. Such disorientation will cause intense pain and render a patient immobile.

It would be desirable, therefore, to provide a prosthesis disc for insertion in the spine of a patient which can be inserted in the middle or lower back and which will not disassemble by the movements of the patient's body.

SUMMARY OF THE INVENTION

Briefly, the present invention is embodied in an intervertebral disc prosthesis for replacement of a disc between an upper vertebrae and a lower vertebrae. The disc prosthesis has a lower member having a lower mounting surface for attachment against an upper surface of a lower vertebrae and an upper member having an upper surface for attachment against a lower surface of an upper vertebrae.

A generally spherical pivot ball on a post extends either upwardly from the upper surface of the lower member or extends downwardly from the lower surface of the upper member. The spherical pivot ball is received in a generally spherical pivot socket on the other of the upper or lower member. In accordance with the present invention, a retaining collar is provided to retain the ball in the socket such that the ball cannot become disoriented with respect to the socket.

Extending along the upper surface of the upper member are a plurality of small pins positioned to extend a short distance within the lower surface of the upper vertebrae against which it is to be fitted. Similarly, the lower surface of the lower member also has a plurality of small pins to be received in the upper surface of the lower member against which it is to be fitted, such that the members will not move with respect to the vertebrae. To retain the upper and lower members against their respective vertebrae, each of the upper and lower members have at least one generally vertically oriented transverse hole through which a screw is fitted, thereby retaining the members to the adjacent vertebrae.

Between the upper and lower members and surrounding the post and pivot ball is an annular resilient cushion member which absorbs shock between the adjacent vertebrae. Also, a tubular shield of flexible material extends around the circumference of the prosthesis to prevent bodily tissues from growing between the members.

Furthermore, the prosthesis of the present invention has outer dimensions which are approximately two-thirds the outer dimensions of the load-bearing portions of the vertebrae between which the prosthesis is to be inserted. The reduced size of the outer dimensions of the prosthesis disc permit a surgeon to install the prosthesis by inserting it in the patient's back, rather than inserting it through the abdomen. Furthermore, the plurality of L-shaped tools with the flattened short ends thereof positioned at different angles with respect to the axis of that short leg provides the surgeon with a plurality of tools which can be interchanged to tightened the screw.

BRIEF DESCRIPTION OF THE DRAWINGS

A better understanding of the present invention will be had after a reading of the following detailed description taken in conjunction with the accompanying drawings wherein.

DETAILED DESCRIPTION OF A PREFERRED EMBODIMENT

Figure 1:
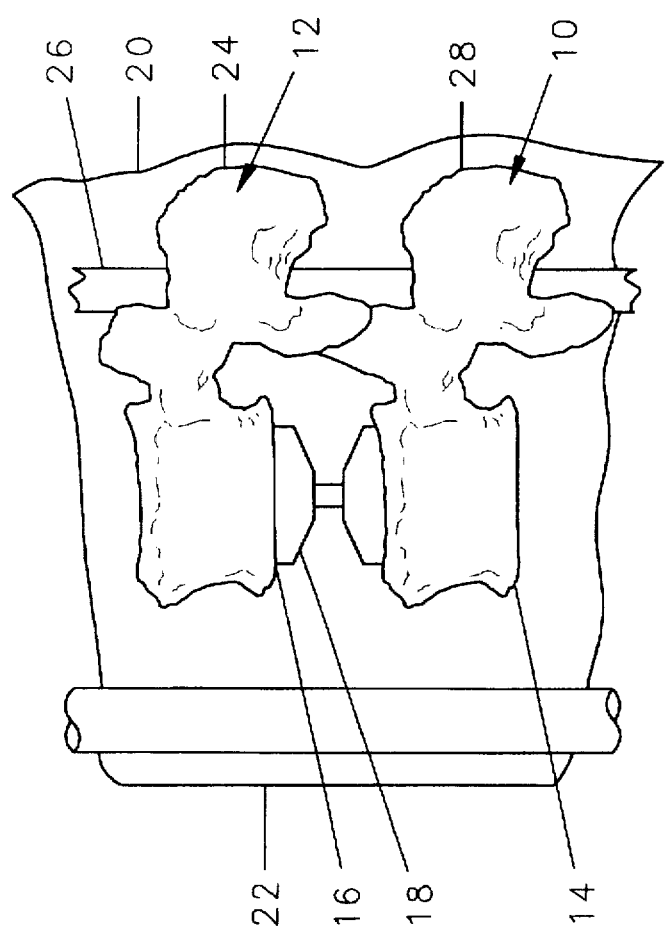
FIG. 1 is a cross-sectional side view of an upper and lower vertebrae of a patient with a prosthesis disc in accordance with the present invention inserted therebetween.

Referring to FIG. 1, the vertebrae of the back are arranged in vertically stacked relationship with a lower vertebrae 10 and an upper vertebrae 12 being representative of two successive vertebrae in the middle or lower portion of the human spine. The lower vertebrae 10 has a generally cylindrical weight-bearing portion 14, and the upper vertebrae 10 has a similar, generally cylindrical weight-bearing portion 16, and between the weight bearing portions 14, 16 are compressible discs. The compressible disc between the successive vertebrae 10, 12, has been removed and replaced by a prosthesis disc 18 in accordance with the present invention.

The vertebrae 10 and 12 are positioned between the skin of the back 20 and the inner wall 22 of the abdominal cavity. Extending toward the back 20 from the weight bearing portion 14 of the lower vertebrae 10 is an annular structure of bone 24 through which the spinal cord 26 extends. Similarly, rearward of the weight bearing portion 16 of the upper vertebrae 12 is a second annular bony structure 28 through which the spinal cord 26 also extends. Adjacent the inner wall 22 of the abdominal cavity are two arteries which extend to the legs, one of which 30 is visible.

Figure 2:
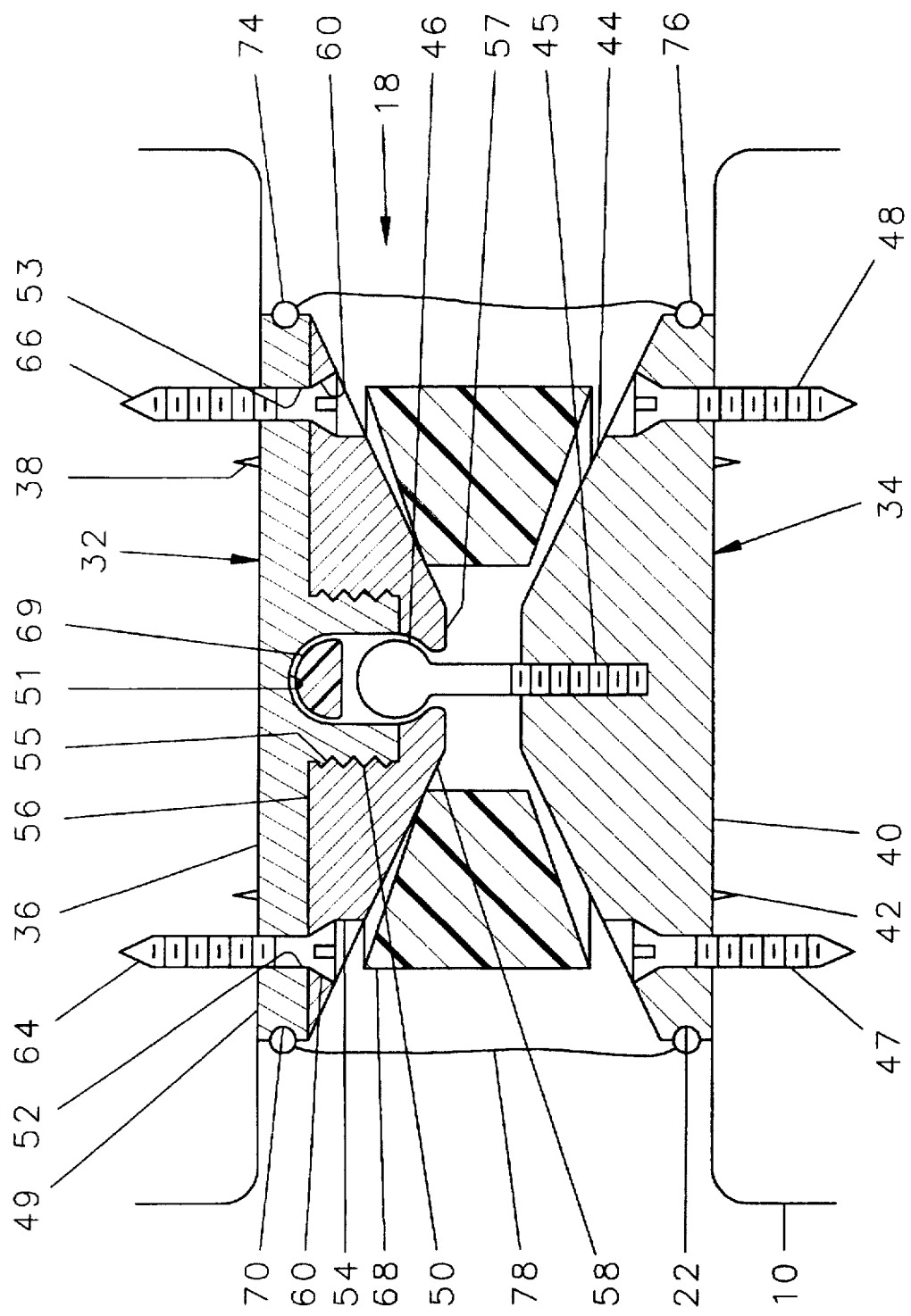
FIG. 2 is an enlarged cross-sectional view of the prosthesis of the present invention.

Referring to FIG. 2, the prosthesis disc 18 of the present invention includes an upper member 32 and a lower member 34. The upper member 32 has a generally planar upper surface 36 from which a plurality of small pins 38 extend into the lower surface of upper vertebrae 12 to retain the prosthesis disc 18 against lateral movement with respect to the upper vertebrae. Similarly, the lower surface 40 of the lower member 34 has a second plurality of pins 42 which extend into the upper surface of the lower vertebrae 10 to retain the prosthesis disc 18 against lateral movement with respect to the lower disc 10.

The lower member 34 has a frustoconically shaped upper surface 44, and threaded vertically into a vertical threaded hole in the center of the frustoconical portion 44 is a threaded post 45 having a generally spherical upper end 46. The lower member 34 is retained against the upper surface of the lower vertebrae 14 by a pair of screws 47, 48 extending through holes in the outer portions of the body of the member 34.

The upper member 32 has a generally disc shaped base portion 49, and extending downward from the center of the base portion 49 is an axially aligned tubular portion 50. The lower surface 51 of the base portion 49 within the tubular portion is concave as shown. Also, around the outer edge of the base portion 49 are a plurality of mounting holes, two of which 52, 53 are shown.

The outer surface of the tubular portion 50 is threaded, and extending around the tubular portion 50 is an annular collar 54. The collar 54 has a threaded axial hole 55 with threads complementary to the threads on the tubular portion 50, and a planar upper surface 56 such that the upper surface 56 abuts the lower surface of the base portion 49 when the parts are threaded together. The lower end of the axial hole 55 is constricted forming a neck 57 and the diameter of the neck 57 is smaller than the diameter of the spherical upper end 46 of the post 45, such that the collar 54 will retain the spherical upper end 46 within the central cavity of the tubular portion 50. The lower surface 58 of the collar 54 is frustoconical as shown, and around the outer circumference thereof are a plurality of countersunk holes 60, two of which are visible.

When the collar 54 is assembled to the base 49, a pair of diametrically opposing holes 60 in the collar 54 can be aligned with the holes 52, 53 in the base 49 and the assembled member 32 is retained to the upper vertebrae 12 by a second pair of screws 64, 66.

Extending around the post 45 and between the frustoconical surfaces 44, 58 of the upper and lower members is an annular shock absorbing member 68. The shock absorbing member 68 has upper and lower surfaces which are frustoconical and generally conform to the adjacent frustoconical surfaces of the upper and lower members as shown.

As can be seen, the cavity within the tubular portion 50 is horizontally elongated such that the pivot ball 46 may move vertically within the cavity between the upper surface 51 and the neck 57. In the preferred embodiment, the shock absorbing member 68 has a thickness at least equal to the distance between the frustoconical surfaces 44, 58 when the pivot ball 46 is positioned against the neck 57 of the retainer 54. When the parts are in this configuration, forces between the upper and lower surfaces 36, 40 of the prosthesis 10 will cause the pivot ball to move upward within the cavity of the tubular portion 50 until it makes contact with the lower surface 51 of the base portion 49, thereby compressing the shock absorbing member 68 and absorbing shock. A shock absorbing plug 69 can also be inserted in the cavity retaining the ball 46 to provide additional shock absorption between the parts.

The base portion 49 has an annular groove 70 around the outer circumference thereof, and around the circumference of the lower member 34 is a second annular groove 72. Fitted into the grooves 70, 72 are first and second retaining rings 74, 76, respectively, and extending between the retaining rings 74, 76 is a tubular membrane 78. Until the prosthesis 10 is inserted in a patient, at least one of the retaining rings 74, 76 must be disconnected from the associated groove 70, 72 to permit installation of the screws.

A surgeon inserting a prosthesis disc 18 will make an incision in the back of a patient and insert the prosthesis 18 around the spinal cord 26 and between the upper and lower vertebrae 10, 12, respectively. Once the prostheses 18 is properly positioned between the vertebrae, he will tighten the screws in place using a right angle drilling tool.

After the upper and lower members 32, 34 are screwed to the upper and lower vertebrae 10, 12, the retaining rings 74, 76 retaining the membrane 78 can be snapped in position.

Figure 3:
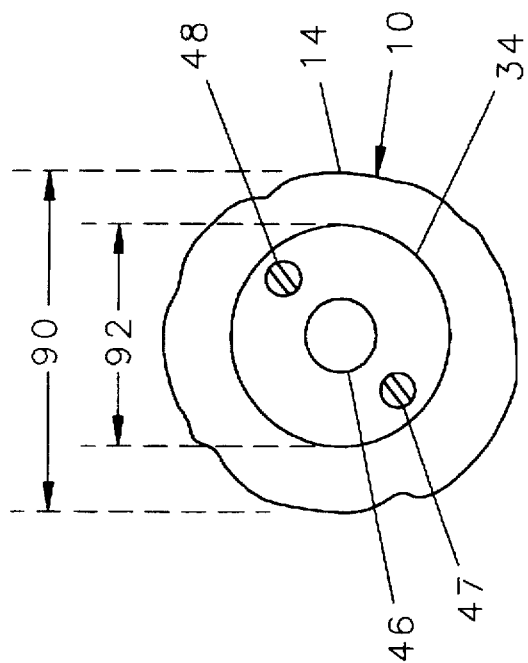
FIG. 3 is a top view of the lower member of the prosthesis shown in FIG. 1 fitted against a lower vertebrae.

Referring to FIG. 3, it can be seen that the weight bearing portion 14 of the lower vertebrae 10 has an outer diameter 90 which is substantially larger than the outer diameter 92 of the lower member 34. In the preferred embodiment, the diameter 92 of the lower member 34 is approximately two-thirds of the outer diameter 90 of the load bearing portion 14 of lower vertebrae 10. Similarly, the outer diameter of the upper disc member 32 is approximately two-thirds of the outer diameter of the load bearing portions 16 of the upper vertebrae 12. The reduced outer diameter of the prosthesis disc 18 permits the disc to be inserted through the back of the patient rather than requiring its insertion through the inner wall 22 of the abdominal cavity.

While one embodiment of the present invention has been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. An intervertebral disc protheses for replacement of a disc between an upper vertebrae and a lower vertebrae comprising, a lower member having a lower mounting surface for attachment against an upper surface of said lower vertebrae, said lower member having an upper surface, an upper member having an upper mounting surface for attachment against a lower surface of said upper vertebrae, said upper member having a lower surface, a pivot ball extending from a post from one of said upper member and said lower member, the other of said upper member and said lower member having an elongate cavity therein, means on said other of said upper member and said lower member for retaining said pivot ball in said cavity, an elastomeric shock absorbing member between said upper member and said lower member, said elastomeric shock absorbing member compressible between a relief condition wherein said upper surface of said lower member has a first spacing from said lower surface of said upper member, and a compressed condition wherein said upper surface of said lower member has a second spacing from said lower surface of said upper member, said second spacing being less than said first spacing, and said pivot ball is vertically movable within said elongate cavity to permit compression of said shock absorbing member from said relief condition to said compressed condition.

2. An intervertebral disc in accordance with claim 1 and further comprising, one of said upper member and said lower member having an annular groove around the circumference thereof, a retaining ring sized for insertion in said groove, and a tubular membrane attached to said retainer ring.

3. An intervertebral disc in accordance with claim 1 wherein, said means for retaining said pivot ball in said cavity including an annular retainer having a central opening with a diameter less than a diameter of said pivot ball.

4. An intervertebral disc prostheses for replacement of a disc between an upper vertebrae and a lower vertebrae comprising, a lower member having a lower mounting surface for attachment against an upper surface of said lower vertebrae, an upper member having an upper mounting surface for attachment against a lower surface of said upper vertebrae, one of said upper member and said lower member have a base portion with a tubular central portion having an inner diameter, an annular collar around said tubular central portion, said annular collar having a central opening, a pivot ball extending from a post from the other of said upper member and said lower member, said pivot ball having a diameter less than said inner diameter, said central opening of said collar having a diameter which is less than said diameter of said pivot ball whereby said collar retains said pivot ball in said tubular central portion, an elastomeric shock absorbing member between said upper member and said lower member, said elastomeric shock absorbing member movable between a relief condition wherein said upper member has a first spacing from said lower member and a compressed condition wherein said upper member has a second spacing from said lower member, and said pivot ball vertically movable within said tubular central portion of said one of said upper member and said lower member to permit compression of said shock absorbing member from said relief condition to said compressed condition.

5. An intervertebral disc in accordance with claim 4 and further comprising, one of said upper member and said lower member having an annular groove around the circumference thereof, a retaining ring sized for insertion in said groove, and a tubular membrane attached to said retainer ring.

6. An intervertebral disc in accordance with claim 4 and further comprising an elastomeric plug within said tubular central portion.

* * * * *